(12) United States Patent
Stucky et al.

(10) Patent No.: US 9,326,995 B2
(45) Date of Patent: *May 3, 2016

(54) OXIDES FOR WOUND HEALING AND BODY REPAIR

(75) Inventors: Galen D. Stucky, Santa Barbara, CA (US); Todd A. Ostomel, Davis, CA (US); Qihui Shi, Goleta, CA (US); April Sawvel, Santa Barbara, CA (US); Sarah Baker, Pleasanton, CA (US)

(73) Assignee: The Regents of the University of California, Oakland, CA (US)

( * ) Notice: Subject to any disclaimer, the term of this patent is extended or adjusted under 35 U.S.C. 154(b) by 1148 days.

This patent is subject to a terminal disclaimer.

(21) Appl. No.: 11/464,825

(22) Filed: Aug. 15, 2006

(65) Prior Publication Data

US 2007/0154564 A1 Jul. 5, 2007
US 2010/0209531 A2 Aug. 19, 2010

Related U.S. Application Data

(63) Continuation-in-part of application No. 11/398,161, filed on Apr. 4, 2006, now Pat. No. 7,858,123.

(60) Provisional application No. 60/708,206, filed on Aug. 15, 2005, provisional application No. 60/668,022, filed on Apr. 4, 2005.

(51) Int. Cl.
| A61K 33/42 | (2006.01) |
| A61K 33/00 | (2006.01) |
| A61K 33/06 | (2006.01) |
| A61K 33/24 | (2006.01) |
| A61K 33/26 | (2006.01) |
| A61K 33/30 | (2006.01) |
| A61K 45/06 | (2006.01) |
| A61L 24/02 | (2006.01) |
| A61L 26/00 | (2006.01) |

(52) U.S. Cl.
CPC ............. *A61K 33/00* (2013.01); *A61K 33/06* (2013.01); *A61K 33/24* (2013.01); *A61K 33/26* (2013.01); *A61K 33/30* (2013.01); *A61K 33/42* (2013.01); *A61K 45/06* (2013.01); *A61L 24/02* (2013.01); *A61L 26/0004* (2013.01)

(58) Field of Classification Search
None
See application file for complete search history.

(56) References Cited

U.S. PATENT DOCUMENTS

| 2,688,586 | A | 9/1954 | Eberl et al. |
| 2,882,243 | A | 4/1959 | Milton |
| 3,122,140 | A | 2/1964 | Crowe et al. |
| 3,181,231 | A | 5/1965 | Breck |
| 3,366,578 | A | 1/1968 | Michalko |
| 3,538,508 | A | 11/1970 | Young |
| 3,723,352 | A | 3/1973 | Warne et al. |
| 3,979,335 | A | 9/1976 | Golovko et al. |
| 4,373,519 | A | 2/1983 | Errede et al. |
| 4,374,044 | A | 2/1983 | Schaefer et al. |
| 4,514,510 | A | 4/1985 | Alexander |
| 4,525,410 | A | 6/1985 | Hagiwara et al. |
| 4,626,550 | A | 12/1986 | Hertzenberg |
| 4,631,845 | A | 12/1986 | Samuel et al. |
| 4,728,323 | A * | 3/1988 | Matson ................... 604/304 |
| 4,744,805 | A | 5/1988 | Maroulis et al. |
| 4,748,978 | A | 6/1988 | Kamp |
| 4,822,349 | A | 4/1989 | Hursey et al. |
| 4,828,081 | A | 5/1989 | Nordstrom et al. |
| 4,828,832 | A * | 5/1989 | De Cuellar et al. ........ 424/618 |
| 4,911,898 | A | 3/1990 | Hagiwara et al. |
| 4,938,958 | A | 7/1990 | Niira et al. |
| 4,956,350 | A | 9/1990 | Mosbey |
| 5,436,362 | A | 7/1995 | Kondoh et al. |
| 5,474,545 | A | 12/1995 | Chikazawa |
| 5,486,195 | A | 1/1996 | Meyers et al. |

(Continued)

FOREIGN PATENT DOCUMENTS

| CN | 1727011 | 2/2006 |
| EP | 0826822 | 3/1988 |
| EP | 0888783 | 7/1999 |
| EP | 1159972 | 5/2001 |
| EP | 1690553 | 8/2006 |

(Continued)

OTHER PUBLICATIONS

Breck et al. Crystalline Zeolites. I. The Properties of a New Synthetic Zeolite, Type A. Journal of the American Chemical Society, vol. 78, No. 23, Dec. 1956.

(Continued)

*Primary Examiner* — Mina Haghighatian
*Assistant Examiner* — Luke Karpinski
(74) *Attorney, Agent, or Firm* — Rudy J. Ng; Carol L. Francis; Bozicevic, Field & Francis LLP (57) ABSTRACT

The invention provides a homogeneous composition comprising a hemostatically effective amount of a charged oxide, wherein the composition has an isoelectric point, as measured in calcium chloride, below 7.3 or above 7.4. Typically, the charged oxide is selected from the group consisting of silaceous oxides, titanium oxides, aluminum oxides, calcium oxides, zinc oxides, nickel oxides and iron oxides. In some embodiments, the composition further comprises a second oxide selected from the group consisting of calcium oxide, sodium oxide, magnesium oxide, zinc oxide, phosphorus oxide and alumina. In a typical embodiment of the invention, the charged oxide is silaceous oxide, the second oxide comprises calcium oxide and the ratio, by molar ratio, of silaceous oxide to calcium oxide is 0.25 to 15. Optionally, the composition further comprises phosphorous oxide. Also described are methods of making and using such compositions.

14 Claims, 8 Drawing Sheets

(56) References Cited

U.S. PATENT DOCUMENTS

| | | | |
|---|---|---|---|
| 5,556,699 A | 9/1996 | Nira et al. | |
| 5,599,578 A | 2/1997 | Butland | |
| 5,696,101 A | 12/1997 | Wu et al. | |
| 5,716,337 A | 2/1998 | McCabe et al. | |
| 5,725,551 A | 3/1998 | Meyers et al. | |
| 5,801,116 A | 9/1998 | Cottrell et al. | |
| 5,826,543 A | 10/1998 | Raymond et al. | |
| 5,941,897 A | 8/1999 | Meyers | |
| 5,964,349 A | 10/1999 | Odagiri | |
| 5,981,052 A | 11/1999 | Suglyama | |
| 6,037,280 A | 3/2000 | Edwards et al. | |
| 6,060,461 A | 5/2000 | Drake | |
| 6,123,925 A | 9/2000 | Barry et al. | |
| 6,159,232 A | 12/2000 | Nowakowski | |
| 6,187,347 B1 | 2/2001 | Patterson et al. | |
| 6,203,512 B1 | 3/2001 | Farris et al. | |
| 6,251,423 B1 * | 6/2001 | Bradford | 424/443 |
| 6,372,333 B1 | 4/2002 | Sugiyama et al. | |
| 6,428,800 B2 | 8/2002 | Greenspan et al. | |
| 6,450,537 B2 | 9/2002 | Norris | |
| 6,475,470 B1 | 11/2002 | Kayane et al. | |
| 6,481,134 B1 | 11/2002 | Aledo | |
| 6,495,367 B1 | 12/2002 | Isogawa et al. | |
| 6,573,419 B2 | 6/2003 | Nalmer | |
| 6,630,140 B1 | 10/2003 | Grunstein | |
| 6,745,720 B2 | 6/2004 | Rasner et al. | |
| 6,767,550 B1 | 7/2004 | Genin et al. | |
| 6,998,510 B2 | 2/2006 | Buckman et al. | |
| 7,371,403 B2 | 5/2008 | McCarthy et al. | |
| 2002/0197302 A1 | 12/2002 | Cochrum et al. | |
| 2003/0133990 A1 | 7/2003 | Hursey et al. | |
| 2003/0176828 A1 | 9/2003 | Buckman et al. | |
| 2003/0198660 A1 | 10/2003 | Janas | |
| 2003/0199922 A1 | 10/2003 | Buckman | |
| 2003/0208150 A1 | 11/2003 | Bruder et al. | |
| 2004/0005350 A1 | 1/2004 | Looney et al. | |
| 2004/0043053 A1 | 3/2004 | Yu | |
| 2004/0166172 A1 | 8/2004 | Rosati et al. | |
| 2004/0243043 A1 | 12/2004 | McCarthy et al. | |
| 2005/0058721 A1 | 3/2005 | Hursey | |
| 2005/0065214 A1 | 3/2005 | Kronenthal | |
| 2005/0070693 A1 | 3/2005 | Hansen et al. | |
| 2005/0074505 A1 | 4/2005 | Hursey | |
| 2005/0118230 A1 | 6/2005 | Hill et al. | |
| 2005/0137512 A1 | 6/2005 | Campbell et al. | |
| 2005/0143689 A1 | 6/2005 | Ramsey, III | |
| 2006/0007862 A1 | 1/2006 | Sayeedi et al. | |
| 2006/0034935 A1 | 2/2006 | Pronovost et al. | |
| 2006/0078628 A1 | 4/2006 | Koman et al. | |
| 2006/0116635 A1 | 6/2006 | Van Heugten | |
| 2006/0141018 A1 | 6/2006 | Cochrum et al. | |
| 2006/0141060 A1 | 6/2006 | Hursey et al. | |
| 2006/0155235 A1 | 7/2006 | Sawyer | |
| 2006/0172000 A1 | 8/2006 | Cullen et al. | |
| 2006/0211965 A1 | 9/2006 | Horn et al. | |
| 2006/0211971 A1 | 9/2006 | Horn et al. | |
| 2006/0271094 A1 | 11/2006 | Hudson et al. | |
| 2007/0004995 A1 | 1/2007 | Horn et al. | |
| 2007/0031515 A1 | 2/2007 | Stucky et al. | |
| 2007/0104268 A1 | 5/2007 | Seok et al. | |
| 2007/0154509 A1 | 7/2007 | Wilcher et al. | |
| 2007/0154510 A1 | 7/2007 | Wilcher et al. | |
| 2007/0154564 A1 | 7/2007 | Stucky et al. | |
| 2007/0160638 A1 | 7/2007 | Mentkow et al. | |
| 2007/0167971 A1 | 7/2007 | Huey et al. | |
| 2007/0275073 A1 | 11/2007 | Huey et al. | |
| 2008/0097271 A1 | 4/2008 | Lo et al. | |
| 2008/0125686 A1 | 5/2008 | Lo et al. | |
| 2008/0145447 A1 | 6/2008 | Bedard | |
| 2008/0145455 A1 | 6/2008 | Bedard | |
| 2008/0146984 A1 | 6/2008 | Campbell et al. | |
| 2008/0199539 A1 | 8/2008 | Baker et al. | |
| 2008/0254147 A1 | 10/2008 | Huey et al. | |
| 2008/0299226 A1 | 12/2008 | Mentkow et al. | |
| 2008/0317831 A1 | 12/2008 | Lo et al. | |
| 2009/0047366 A1 | 2/2009 | Bedard et al. | |
| 2009/0123525 A1 | 5/2009 | Bedard | |
| 2009/0155342 A1 | 6/2009 | Diegelmann et al. | |
| 2009/0162406 A1 | 6/2009 | Basadonna et al. | |

FOREIGN PATENT DOCUMENTS

| | | |
|---|---|---|
| EP | 1714642 | 10/2006 |
| EP | 1810697 | 7/2007 |
| GB | 2314842 | 1/1998 |
| JP | 61145120 | 7/1986 |
| JP | 3272770 | 4/1991 |
| JP | 4146218 | 5/1992 |
| JP | 11-332909 | 7/1999 |
| JP | 2004123651 | 4/2004 |
| WO | WO 9505445 | 2/1995 |
| WO | WO 9640285 | 12/1996 |
| WO | WO/97/17401 | 5/1997 |
| WO | WO/98/47465 | 10/1998 |
| WO | WO 9913918 | 3/1999 |
| WO | WO/00/09176 A1 * | 2/2000 |
| WO | WO 0066086 | 11/2000 |
| WO | WO/0076486 | 12/2000 |
| WO | WO 0182896 | 8/2001 |
| WO | WO 0230479 | 4/2002 |
| WO | WO 02060367 | 8/2002 |
| WO | WO 02074325 | 9/2002 |
| WO | WO 03074566 | 9/2003 |
| WO | WO 2004005533 | 1/2004 |
| WO | WO/2004/071542 | 8/2004 |
| WO | WO/2004/103421 | 12/2004 |
| WO | WO 2005012493 | 2/2005 |
| WO | WO 2005/027808 A1 | 3/2005 |
| WO | WO/2005/027808 A1 | 3/2005 |
| WO | WO 2005027808 | 3/2005 |
| WO | WO 2005087280 | 9/2005 |
| WO | WO/2006/012218 A1 | 2/2006 |
| WO | WO 2006012218 | 2/2006 |
| WO | WO 2006088912 | 8/2006 |
| WO | WO2006088912 | 8/2006 |
| WO | WO 2006102008 | 9/2006 |
| WO | WO2006110393 | 10/2006 |
| WO | WO 2007022264 | 2/2007 |
| WO | WO 2007120342 | 10/2007 |
| WO | WO 2008017203 | 2/2008 |
| WO | WO 2008036225 | 3/2008 |

OTHER PUBLICATIONS

Hench et al. "Bonding Mechanisms at the Interface of Ceramic Prosthetic Materials," J. Biomed. Mater. Res. Symposium, No. 2 (Part 1) pp. 117-14, 1971.

Mineral Herbal Medicine, edited by Lanzhong Guo, 1995, pp. 59-61.

Wright, James K., et al., "Thermal Injury Resulting from Application of a Granular Mineral Hemostatic Agent", Aug. 2004, The Journal of Trauma, 57(2).

Saravanapavan, P., et al., "Low-temperature Synthesis, Structure, and Bioactivity of Gel-derived . . . system", Mar. 2001, J. Biomed Mater Res., 54(4):608-18 (1pg Abstract only).

Sepulveda, Pilar, et al., "Bioactive Sol-gel Foams for Tissue Repair", Center for Tissue Engineering and Repair, London/UK, John Wiley & Sons, Inc. Jun. 2001, p. 340-348.

Dyer, A., et al. Diffusion in heteroionic zeolites: part 1—Diffusion of water in heteroionic natrolites. Microporuous and Mesoporous Materials. 1998, vol. 21, pp. 27-38.

Top, A., et al. Silver, zinc, and copper exchange in a Na-clinoptilolite and resulting effect on antibacterial activity. Applied Clay Science. 2004, vol. 27, pp. 13-19.

Wright, J. K., et al. Thermal injury resulting from application of a granular mineral hemostatic agent. The Journal of Trauma Injury, Infection and Critical Care. 2004, vol. 57, No. 2, pp. 224-230.

Abe, Y., et al. Effect of saliva on an antimicrobial tissue conditioner containing silver-zeolite. Journal of Oral Rehabilitation. 2004, vol. 31, pp. 568-573.

Acheson, E., et al. Comparison of hemorrhage control agents applied to lethal extremity arterial hemorrhages in swine. Journal of Trauma Injury, Infection and Critical Care. 2005, vol. 59, pp. 865-875.

(56) References Cited

OTHER PUBLICATIONS

Ahuja, N., et al. Testing of modified zeolite hemostatic dressings in a large animal model of lethal groin injury. Journal of Trauma Injury, Infection and Critical Care. 2006, vol. 61, pp. 1312-1320.

Alam, H., et al. Comparative analysis of hemostatic agents in a swine model of lethal groin injury. Journal of Trauma Injury, Infection and Critical Care. 2003, vol. 54, pp. 1077-1082.

Alam, H. et al. Application of a zeolite hemostatic agent achieves 100% survival in a lethal model of complex groin injury in swine. Journal of Trauma Injury, Infection and Critical Care. 2004, vol. 56, pp. 974-983.

Alam, H., et al. Hemorrhage control in the battlefield: role of new hemostatic agents. Military Medicine. 2005, vol. 170, pp. 63-69.

Browne, J., et al. Characterization and adsorptive properties of pharmaceutical grade clays. Journal of Pharmaceutical Sciences. 1980, vol. 69, No. 7, pp. 816-823.

Davie, E., et al. The coagulation cascade: initiation, maintenance and regulation. Biochemistry. 1991, vol. 30, No. 43, pp. 10363-10370.

Drebushchak, V., et al. Measurements of heat of zeolite dehydration by scanning heating. Journal of Thermal Analysis and Calorimetry. 1999, vol. 58, pp. 653-662.

Hench, L., et al. Bioceramics. Journal of the American Ceramic Society. 1998, vol. 81, No. 7, pp. 1705-1728.

Hoffman, M., et al. Remodeling the blood coagulation cascade. Journal of Thrombosis and Thrombolysis. 2003, vol. 16, pp. 17-20.

Huo, Q., et al. Generalized synthesis of periodic surfactant/inorganic composite materials. Nature. 1994, vol. 368, pp. 317-321.

Jalilehvand, F., et al. Hydration of the calcium ion. An EXAFS, large-angle x-ray scattering, and molecular dynamics simulation study. Journal of the American Chemical Society. 2001, vol. 123, pp. 431-441.

Kawahara, K., et al. Antibacterial effect of silver-zeolite on oral bacteria under anaerobic conditions. Dental Materials. 2000, vol. 16, pp. 452-455.

Kheirabadi, B., et al. Hemostatic efficacy of two advanced dressing in an aortic hemorrhage model in swine. Journal of Trauma Injury, Infection and Critical Care. 2005, vol. 59, pp. 25-35.

Koper, O., et al. Alkaline-earth oxide nanoparticles obtained in aerogel methods. Characterization and rational for unexpectedly high surface chemical reactivities. Chemistry of Materials. 1997, vol. 9, pp. 2468-2480.

Lu, H., et al. Surface characterization of hydroxyapatite and related calcium phosphates by XPS and TOF-SIMS. Analytical Chemistry. 2000, vol. 72, pp. 2886-2894.

Mizota, T., et al. Hydration enthalpies of synthetic Na-A, cation-exchanged-A and some natural zeolites for evaluating as heat exchange absorbents. Thermochimica Acta. 1995, vol. 266, pp. 331-341.

Ostomel, T., et al. Host-guest composites for induced hemostasis and therapeutic healing in traumatic injuries. Journal of thrombosis and thrombolysis. 2006, vol. 22, pp. 55-67.

Ostomel, T., et al. Oxide hemostatic activity. Journal of the American Chemical Society. 2006, vol. 128, pp. 8384-8385.

Ostomel, T., et al. Spherical bioactive glass with enhanced rates of hydroxyapatite deposition and hemostatic activity. Small. 2006, vol. 2, No. 11, pp. 1261-1265.

Perez-Pariente, J., et al. Surface and chemical study of $SiO_2$-$P_2O_5$-CaO-(MgO) Bioactive Glasses. Chemistry of Materials. 2000, vol. 12, pp. 750-755.

Portier, J., et al. Acid-base behavior of oxides and their electronic structure. Solid State Sciences. 2003, vol. 5, pp. 695-699.

Sekiyah, F., et al. Magnesium (II) is a crucial constituent of the blood coagulation cascade. Journal of Biological Chemistry. 1996, vol. 271, No. 15, pp. 8541-8544.

Shimojima, A., et al. Direct formation of mesostructured silica-based hybrids from novel siloxane oligomers with long alkyl chains. Angewandte Chemie. 2003, vol. 42, pp. 4057-4060.

Wolberg, A., et al. A systematic evaluation of the effect of temperature on coagulation enzyme activity and platelet function. Journal of Trauma Injury, Infection and Critical Care. 2004, vol. 56, pp. 1221-1228.

Yang, Y., et al. H NMR spectroscopic evidence of interaction between ibuprofen and lipoproteins in human blood plasma. Analytical Biochemistry. 2004, vol. 324, pp. 292-297.

Yu, B., et al. A thermoanalytical study of dehydration and NaA, MgNaA and SrNaA zeolites. Thermochimica Acta. 1992, vol. 200, pp. 299-308.

Zhao, D., et al. Nonionic triblock and star diblock copolymer and oligomeric surfactant syntheses of highly ordered, hydrothermally stable, mesoporous silica structures. Journal of the American Chemical Society. 1998, vol. 120, pp. 6024-6036.

Carrado, K.A., et al. (2004) "Effects of Surface Functionalization and Organo-Tailoring of Synthetic Layer Silicates on the Immobilization of Cytochrome c" Chem. Mater. 16(13):2559-2566.

Ha, K., et al. (2000) "Facile Assembly of Zeolite Monolayers on Glass, Silica, Alumina, and Other Zeolites Using 3-Halopropylsilyl Reagents as Covalent Linkers" Advanced Materials 12(15):1114-1117.

Jerez, J., et al. (2006) "Coating of Silica Sand with Aluminosilicate Clay" Journal of Colloid and Interface Science 294(1):155-164.

Lin, J.J., et al. (2007) "Preparation of Protein-Silicate Hybrids from Polyamine Intercalation of Layered Montmorillonite" Langmuir 23(4):1995-1999.

Liu, H., et al. (2003) "Synthesis and Characterization of Kaolin/NaY/MCM-41 Composites" Microporous and Mesoporous Materials 66(1):117-125.

Mao, R.L.V., et al. (1993) "Mesoporous Aluminosilicates Prepared from Zeolites by Treatment with Ammonium Fluorosilicate" J. Mater. Chem. 3(6):679-683.

Naskar, M.K., et al. (2008) "Significant Improvement in the Pore Properties of SBA-15 Brought About by Carboxylic Acids and Hydrothermal Treatment" J. Chem. Sci. 120(1):181-186.

Yoon, K.B. (2007) "Organization of Zeolite Microcrystals for Production of Functional Materials" Acc. Chem. Res. 40:29-40.

* cited by examiner

| BG80_Porous | ΔHHYDRATION = 460 J/g | 19% H2O srb |
| --- | --- | --- |
| BG60_Porous | ΔHHYDRATION = 440 J/g | 14% H2O srb |
| BG80_Nonporous | ΔHHYDRATION = 90 J/g | 3% H2O srb |
| BG60_Nonporous | ΔHHYDRATION = 76 J/g | 2% H2O srb |

Summary Report

Area

BET Surface Area: 961.3320 m²/g

Volume

Single Point Desorption Total Pore Volume of pores less than
    195.8471 nm Diameter at P/Po 0.99003125:     0.608964 cm³/g BJH Adsorption Cumulative Pore Volume of pores
    between 1.700000 and 300.000000 nm Diameter:     0.505212 cm³/g Pore Size Desorption Average Pore Diameter (4V/A by BET):     2.5338 nm BJH Adsorption Average Pore Diameter (4V/A):     3.1078 nm

OXIDES FOR WOUND HEALING AND BODY REPAIR

This application is a continuation-in-part of U.S. patent application Ser. No. 11/398,161, filed Apr. 4, 2006, and claims the benefit of provisional patent application Nos. 60/708,206, filed Aug. 15, 2005, and 60/668,022, filed Apr. 4, 2005, the entire contents of each of which is incorporated herein by reference.

GOVERNMENT RIGHTS

This invention was made with Government support under Grant No. N00014-04-1-0654, awarded by the Office of Naval Research. The Government has certain rights in this invention.

Throughout this application various publications are referenced. The disclosures of these publications in their entireties are hereby incorporated by reference into this application in order to more fully describe the state of the art to which this invention pertains.

TECHNICAL FIELD OF THE INVENTION

The invention disclosed herein relates to compositions and methods for modulating the blood coagulation cascade, accelerating bone generation, and assisting in wound healing and body repair. Both the materials selected for the hemostatic composition and the method for regulating hemostasis provide novel means for predictable control over blood coagulation, allowing for both accelerating and slowing or stopping blood flow.

BACKGROUND OF THE INVENTION

U.S. Pat. No. 4,822,349 issued to Hursey, et. al. describes reduction of blood flow by application of a dehydrated zeolite material to the site of blood flow. In this method, a particular calcium rich zeolite formulation of the class Linde Type 5A has been utilized as an external application to a traumatically wounded individual to induce hemostasis through dehydration of the wounded area and induction of a blood clot formation (Breck, D W et al., *J. Am. Chem. Soc.* 78, 23 (1950) 5963.). A major disadvantage to this product has been the excessive heat generated locally at the injured site as a consequence of the large enthalpy of hydration associated with the material currently marketed under the trade name, Quik-Clot™ and distributed by Z-medica corporation of Newington, Conn. USA. There remains a need for modifications and improvements that optimize the enthalpy of hydration upon rehydration of the dehydrated zeolite.

Bioactive glasses (BGs) with $SiO_2$—CaO—$P_2O_5$-MO (M=Na, Mg, etc.) compositions were invented by Hench in 1971 (L. L. Hench et al., *J. Biomed. Mater. Res.* 1971, 2:117) and have been widely studied and used in clinical applications for bone and dental repair due to their chemical bonding with both soft and hard tissue through an apatite-like layer. The apatite-like layer promotes the adhesion of bioactive glass to tissues and avoids the formation of an intervening fibrous layer. This has been shown to decreases the failure possibilities of prostheses and influence the deposition rate of secondary bone and tissue growth. In vivo implantation studies demonstrate that these compositions produce no local or systemic toxicity, are biocompatible, and do not result in an inflammatory response. The $SiO_2$—CaO—$P_2O_5$-MO BG system has been synthesized by the melting-quenching method (Hench et al., 1971, supra) or by the sol-gel method (P. Sepulveda et al., *J. Biomed. Mater. Rev.* 2002, 59:340; P. Saravanapavan and L. L. Hench, *J. Biomed. Mater. Res.* 2001, 54:608). Compared with the traditional melting-quenching method, sol-gel techniques were developed in the past decade to produce the same material at a lower working temperature. Sol-gel techniques also allow a greater degree of functionalization to be incorporated into the bioactive glass material to increase the rate of apatite-like layer growth as well as afford a wider range of bioactivity.

SUMMARY OF THE INVENTION

The invention provides a homogeneous composition comprising a hemostatically effective amount of a charged oxide, wherein the composition has an isoelectric point, as measured in a calcium chloride solution, below 7.3 or above 7.4. Typically, the charged oxide is selected from the group consisting of silaceous oxides, titanium oxides, aluminum oxides, calcium oxides, zinc oxides, nickel oxides and iron oxides. In some embodiments, the composition further comprises a second oxide selected from the group consisting of calcium oxide, sodium oxide, magnesium oxide, zinc oxide, phosphorus oxide and alumina. In a typical embodiment of the invention, the charged oxide is silaceous oxide, the second oxide comprises calcium oxide and the ratio, by molar ratio, of silaceous oxide to calcium oxide is 0.25 to 15. Optionally, the composition further comprises phosphorous oxide. Unlike conventional silaceous oxide compositions, the composition of the invention can be free of sodium oxide.

The charged oxide can be porous or nonporous. In some embodiments, the charged oxide comprises glass beads that are from about 10 nm to about 100 microns in diameter, typically from about 3 to about 10 microns in diameter. In some embodiments, the oxide is a layered clay such as the aluminosilcate Kaolin. In some embodiments, the charged oxide is porous, having pores of 2-100 nm diameter, typically 100-200 μm diameter. The greater the porosity, the greater the surface area. The internal surface area can be between 1 and 1500 square meters per gram as determined by BET $N_2$ adsorption. While non-porous bioactive glass typically has a surface area around 20-30 square meters per grain, mesoporous bioactive glass is distinct because its surface area is greater than 200 square meters per gram. In a typical embodiment, the surface area is between 300 and 1000 square meters per gram.

Additional components that can be included in a composition of the invention include a zeolite and/or an inorganic salt. Examples of an inorganic salt include, but are not limited to, a divalent ion selected from the group consisting of zinc, copper, magnesium, calcium and nickel, as well as the following. CaO, $CaCl_2$, $AgNO_3$, $Ca(NO_3)_2$, $Mg(NO_3)_2$, $Zn(NO_3)_2$, $NH_4NO_3$, AgCl, $Ag_2O$, zinc acetate, magnesium acetate, calcium citrate, zinc citrate, magnesium citrate, magnesium chloride, magnesium bromide, zinc chloride, zinc bromide, calcium bromide, calcium acetate and calcium phosphate.

In some embodiments, the charged oxide is hydrated to between 0.1% and 25%, typically between 0.5% and 5% w/w. The composition of the invention can be prepared as a sol-gel. In some embodiments, the composition further comprises an ammonium phosphate buffer.

The invention additionally provides a method of modulating hemostasis comprising contacting blood with a composition described herein. The modulating can comprise decreasing blood coagulation time, for which purpose the composition has an isoelectric point below 7.3. Examples of materials with an isoelectric point below 7.3 include, but are not limited to, silaceous oxides, titanium oxides, and aluminosilicates. Alternatively, the modulating comprises increasing blood coagulation time and the composition has an isoelectric point above 7.4. Examples of materials with an isoelectric point above 7.4 include, but are not limited to, $Al_2O_3$ and related aluminum oxides, calcium oxides, zinc oxides, nickel oxides, and magnetite and related iron oxides.

Also provided is a method of preparing a hemostatic composition. The method comprises: co-assembling a bioactive glass sol with a structure-directing amount of a triblock copolymer of poly(ethylene oxide)-poly(propylene oxide)-poly(ethylene oxide) to form a gel; and calcining the gel so produced at a temperature sufficiently high to remove the block copolymer and form mesopores; wherein the bioactive glass has all isoelectric point below the pH of blood. Similarly, the invention provides a method of preparing a passivated surface composition for minimizing coagulation upon contact of blood with the surface. The method comprises co-assembling a bioactive glass sol with a structure-directing amount of a triblock copolymer of poly(ethylene oxide)-polypropylene oxide)-poly(ethylene oxide) to form a gel; and calcining the gel produced in step (a) at a temperature sufficiently high (typically 300-700° C.) to remove the block copolymer, form mesopores and create a highly hydroxylated surface; wherein the bioactive glass has an isoelectric point above the pH of blood.

In addition, the invention provides a method of preparing a hemostatic composition. This method comprises passing a carrier gas through a solution comprising a bioactive glass sol to produce droplets; and spraying the droplets down a furnace. Examples of a carrier gas include, but are not limited to, air, nitrogen, oxygen, or natural gas. In some embodiments, such as for preparation of mesoporous materials, the solution further comprises a block copolymer.

In another embodiment, the invention provides a method of preparing a hemostatic composition of micropores. The method comprises cooling a solution comprising silicic acid and calcium salts to below 0° C. to form a gel; and freeze-drying the gel to form micropores. Typically, the cooling step comprises cooling the solution to −70° C. to −200° C. In some embodiments, the solution further comprises a phosphorous oxide, typically in the form of a phosphate group. In another embodiment, the solution further comprises chitosan. The method can further comprise calcining the gel at 300 to 900° C. In a typical embodiment, the cooling comprises direction freezing. In some embodiments, the micropores produced by the method are 1 to 200 microns in diameter.

The invention further provides a method of modulating hemostasis comprising contacting blood with a composition prepared by one of the methods described herein. In addition, the invention provides a medical device that has been coated with a composition of the invention, such as a composition having an isoelectric point above the pH of blood.

Also provided is a method of promoting the formation of tissue comprising contacting the composition of the invention with a hydroxyapatite precursor solution. The tissue can comprise, for example, artificial bone, artificial skin, or a component thereof.

DETAILED DESCRIPTION OF THE INVENTION

The invention is based on the discovery that oxide materials can be prepared to modulate hemostasis on the basis of surface charge. This modulation enables the synthesis of materials that are pro-coagulants; or, alternatively other materials that are anticoagulants. The latter are of importance with respect to die oxide coatings that form on metal medical implant devices. The methods of preparing oxide compositions of the invention avoid problems associated with longer setting times and also produce materials having better performance characteristics. The methods of the invention produce materials that offer superior compositional and structural homogeneity and higher surface area, which provide more effective materials. For example, one embodiment of the invention provides a rapid-setting, mesoporous, bioactive glass cement that exhibits excellent plasticity, superior bioactivity and is mechanically robust. In addition to modulation of hemostasis, the oxide compositions of the invention can be used for growth and repair of bone and other tissues as well as in drug delivery.

In one embodiment of the invention, high surface area mesoporous bioactive glass has been prepared by a sol-gel template directed assembly. This material has the ability to conform and adhere to wounded tissue to promote blood clot formation. This specific material has a distinct morphological advantage over previous bioactive glass materials in that it can conform and adhere to any wound cavity geometry. When mixed with an ammonium phosphate buffer solution, a bioactive glass cement can be formulated that has a predictable set time and accelerates the deposition of new apatite, layers when in contact with biological fluids. Mesoporous bioactive glass (MBG) cements are malleable before setting and retain their shape and mechanical strength without crumbling after setting. Furthermore, mesoporous bioactive glass has demonstrated a high osteoconductive property. This material can be formulated in a variety of compositions for applications as a rapid acting hemostatic agent, template for the growth of artificial bone, and the generation of tissue. Bioactive glass can be formulated for a variety of distinct wound healing scenarios and can elicit a predictable wound healing response, for both controlling the flow of blood as well as controlling the rate of apatite deposition, as a function of agents chemical composition and Si to Ca ratio.

In addition to the synthesis of mesoporous bioactive glass, this invention provides a method by which materials can be selected based on their isoelectric point to induce a predictable hemostatic response. Under physiological conditions, the isoelectric point of an oxide will determine both the sign and magnitude of the initial surface charge density upon exposure to biological fluids. Oxides have been identified that will induce coagulation upon exposure to blood. Oxides have also been identified that will prevent or slow down the coagulation response of blood in contact with the surface of the oxide. A strategy to produce both rapid acting hemostatic agents and passivated medical device surfaces is described based on the selection criteria.

Definitions

All scientific and technical terms used in this application have meanings commonly used in the art unless otherwise specified. As used in this application, the following words or phrases have the meanings specified.

As used herein, a "hemostatically effective amount" means an amount sufficient to initiate detectable blood clotting (R) within 2 minutes, and/or achieve a rate of clotting ($\alpha$) of $50°$ or greater, and/or achieve a clot strength (MA) of $\geq 50$, as determined by Thromboelastograph® measurements. Assays for determining hemostatic effectiveness are known in the art, and described in die Examples below.

As used herein, a "Thromboelastograph" assay refers to measurements typically taken using about 5-30 mg of material mixed with 340 microliters of citrate stabilized blood. Calcium ions are re-supplied to the citrate stabilized blood prior to measurements to replace the calcium ions chelated by citrate.

As used herein, "isoelectric point" refers to the pH at which the zeta-potential equals zero in an aqueous electrolyte such as 2 mM $CaCl_2$. The zeta potential is the surface charge density of a metal oxide in aqueous suspension, measured as a function of pH by the electrophoretic method using the Smoluchowski equation (Cocera, M. et al., *Langmuir* 1999, 15, 2230-2233). Unless specifically indicated otherwise, the zeta potential of the metal oxide is measured in a $CaCl_2$ electrolyte that mimics the $Ca^{2+}$ concentration in blood.

As used herein, "homogeneous" means an absence of phase separation (e.g., separation of a silicate phase and a phosphate phase); the materials are not phase segregated when examined by energy-dispersive x-ray analysis (EDX) using scanning electron microscopy (SEM) with a resolution limit of 0.5 microns. A composition is homogeneous if it consists of a uniform distribution or dispersion of components.

As used herein, a "bioactive glass sol" means a colloidal suspension containing silica precursors and calcium salts that can be gelled to form bioactive glass solid, wherein the solvent can be water, ethanol or other substance that can dissolve silica precursors and calcium species.

As used herein, "a" or "an" means at least one, unless clearly indicated otherwise.

Bioactive Glass (BG)

For the sol-gel-derived BGs to exhibit in vitro bioactive behavior, it has been shown that both the chemical composition and textural properties (pore size and volume) are important. Melt-derived glasses show a direct dependence on composition with bioactivity. Increasing the specific surface area and pore volume of BGs will greatly accelerate the kinetic deposition process of hydroapatite and therefore enhance the bone-forming bioactivity of BGs. Several strategies have been developed to obtain high specific surface area materials and engineer pore stricture of the BGs, including using soluble inorganic salt, colloidal spheres or block copolymers as pore-forming agents. The high surface area mesoporous bioactive glass described herein has a unique morphology with advantages over these methods including higher surface area and ease of functionalization of the final material. This functionalization includes, but is not limited to, the surface immobilization and the controlled release of biologically relevant molecules. Molecules such as phospholipids, fibrin, collagen, clotting zymogens, heat shock proteins, antibacterial peptides, and silver, magnesium, calcium, sodium, zinc, chloride, and phosphate ions can be controllably released to effect an optimal bio-response.

The porous bioactive glass material can be described by the general formula $SiO_2$—$CaO$—$P_2O_5$-MO (M=Na, Mg, etc.). BET analysis has shown that the bioactive glass of the invention has a surface area far greater than the 5 square meters per gram ($m^2/g$) observed in prior art materials, and typically in the range of more than 100 $m^2/g$, often more than 200 $m^2/g$. In one embodiment, the bioactive glass of the invention has a surface area of at least about 300 $m^2/g$. Surface areas of 500-1000 $m^2/g$ can be attained. The surface area is influenced by the polymer used in synthesis of the bioactive glass. A surface area of about 300 $m^2/g$ has been attained with bioactive glass prepared from P123, while low molecular weight polymers, such as L43, can produce much higher surface area (in the range of 900 $m^2/g$). The high surface area provides for optimal pore volume.

Hemostatic Activity of Bioactive Glass

Disclosed herein is a new and specific application of bioactive glass related to rapid acting hemostatic agents for the treatment of traumatic injuries. The traumatic wound healing scenario is distinct from prior medical applications for bioactive glass-like materials. The term "bioactive glass" has been loosely applied to many composites of calcium oxide, silicon dioxide, phosphorous oxide and other metal oxides, the combination of which is able to promote the growth of bone and tissue.

The invention described in U.S. provisional patent application No. 60/668,022, filed Apr. 4, 2005, provides a calcium loaded zeolite linde type A that is ion exchanged with aqueous solutions of alkali, alkaline earth, and transition metal cations to specific ion formulations. This ion exchanged zeolite can be mixed with neutral inorganic salts like calcium chloride, aluminum sulfite, and silver nitrate and dehydrated to remove water. The dehydrated inorganic materials are sealed in mylar foil bags to prevent rehydration until required during medical application. At the time of medical application, the mylar bag can be opened and the inorganic contents poured into the traumatically injured site.

The present invention provides the bioactive glass in a gel) liquid, cement, paste or powder form, which allows for greater ease of use and better conformation to a desired area to be treated. By providing the material in gel (or cement) form, for example, it can be applied to a greater variety of surfaces, increasing its availability for use in numerous contexts, including application to medical devices and drug delivery.

Porous bioactive glass materials have been designed to treat traumatically injured tissue by inducing hemostasis through contact activation and release of coagulation co-factors. In addition, the compositions of the present invention provide a uniform pore size that further optimizes its use for regulation of hemostasis.

The hemostatic activity of bioactive glass is dependent on the material's chemical composition. For the range of chemically distinct bioactive glass agents studied (Si:Ca:$P_{atomic\_ratio}$ 60:36:4 to 90:6:4), the onset time for contact-activated coagulation, rate of coagulation of post-initiation, and ultimate clot strength was found to be dependent on the material's Si:Ca ratio, porosity, and heat of hydration. The onset time for contact-activated coagulation was found to decrease in an increasing Si:Ca ratio.

The rate of coagulation post-initiation was found to increase with an increasing Si:Ca ratio. Porous bioactive glass was found to have a greater procoagulant tendency than non-porous bioactive glass.

Bone-generating Activity of Bioactive Glass

The bone-generating activity of bioactive glass is dependent on the material's chemical composition. For the range of chemically distinct bioactive glass agents studied, (Si:Ca:$P_{atomic\_ratio}$ 60:36:4 to 90:6:4) the deposition rate of hydroxyapatite deposition in biological fluids is related to the material's Si:Ca ratio and particle size and shape. The rate of deposition of hydroxyapatite was observed to be faster for bioactive glass samples with a lower Si:Ca ratio (e.g. BG60:36:4 faster than BG80:16:4).

The high osteoconductive properties of this unique formulation of bioactive glass is a result of the presence of a large number of surface hydroxyl groups (Si—OH) that provide nucleation sites for apatite-like layer growth. The sol-gel technique developed in our laboratory allows us to optimize these nucleation sites for a tailored bio-response, and ultimately an improved generation of hydroxyapatite.

The Isoelectric Point Material Property as a Predictor of Hemostatic Activity

The isoelectric point of a material is a critical material parameter that can be utilized to select oxides that can either promote or prevent the induction of hemostasis. Rapid acting hemostatic agents and passivated medical devices are applications intended for this material. The present inventors have discovered that the oxide's initial surface charge, driven by the isoelectric point of the material relative to the pH of the immersing biological medium, is the key factor in controlling hemostatic efficacy of the composition.

The onset time for contact-activated coagulation, rate of coagulation post-initiation, and ultimate clot strength are found to be dependent on the initial surface charge density of the metal oxide when exposed to blood, which is related to the oxide's acid-base nature and is quantitatively described by its isoelectric point. Wee found, that for polar metal-oxide substrates, the time to initiate contact-activated coagulation increases with the increase in the metal oxide's isoelectric point.

Blood is usually the first fluid an implanted foreign body encounters, and thus the thrombotic complications which arise from metallic implants (chronic inflamatory response), and inorganic-based extracorporeal circulating devices parts, arterial stents, and catheters is related to the chemistry that occurs during the initial exposure of blood to a foreign oxide surface. Although the activating inorganic surface will become contaminated with biological products over time (e.g. massive attack complex, fibrin[12]), the initial surface charge density of a metal oxide surface will affect the selective adhesion of oppositely charged molecules and biological media (e.g. cells and larger proteins) immediately upon contact with blood. We observed that both the sign and magnitude of the metal oxide's surface-charge density affects blood coagulation metrics, including the onset time, rate of clot formation, and viscoelastic strength of contact-activated blood clots, and that an oxide's isoelectric point can be used to predict its in vitro hemostatic activity.

Negatively-charged surfaces are known to initiate the intrinsic pathway of the blood coagulation cascade, a network of feedback-dependent reactions that when activated results in a blood clot. The activation of this process by a foreign body is referred to as contact-activation of coagulation. The same network of coagulation reactions also can be activated via the extrinsic pathway, which occurs when a breach in the endothelium allows the exposure of platelets to tissue factor bearing cells.

Because of the electronegativity difference between oxygen atoms and the metallic atoms they are covalently bonded to, metal oxides are inherently polar surfaces. Their surface chemistry is all the more complicated due to the presence of "dangling" terminal hydroxyl groups on unsaturated metal sites and related defect sites. The surface charge of metal oxides is known to be pH dependent and is thought to result from either the amphoteric dissociation of surface MOH groups or the adsorption of metal hydroxo complexes derived from the hydrolysis product of material dissolved from the metal oxide. There exists a unique pH for each oxide above which the material is negatively charged and below which the material is positively charged. The pH at which the sum total of negative and positive surface charges equals zero, $\Sigma(z-n) M^{z+}(OH)_n^{z-n}=0$, is called the isoelectric point.

We have observed a variable contact-activated coagulation response from metal oxides with distinct isoelectric points, all of which are inherently polar substrates, and which requires that we refine our understanding of the traditional definition of hemocompatibility based on surface energetics. We have found that acidic oxides are prothrombotic while basic oxide are antithrombotic. The relative difference between the metal-oxide's isoelectric point and the pH of blood determines the initial surface-charge density of the substrate when exposed to blood. This material parameter has been shown to affect the onset time for coagulation, rate of coagulation post-initiation, and ultimate clot strength.

Thromboelastograph Assay

Thromboelastograph®. The in vitro hemostatic activity of metal-oxide hemostatic agents was evaluated as previously described using a Thromboelastograph®, a clinical instrument that monitors the change in viscoelasticity of blood as a function of time. Briefly, 340 µL of 4% v/v citrate-stabilized sheep blood (Quad Five of Ryegate, Mont.) was introduced into the sample cup of a Thromboelastograph®, Haemoscope model 5000, along with 20 µL of 0.2M $CaCl_2$(aq) and 5-20 mg of a tested metal-oxide in a powder morphology. The 20 µL of 0.2 M $CaCl_2$(aq) was added to the stabilized blood to replenish the $Ca^{2+}$ ions chelated by citrate, which was added to prevent coagulation of stored blood. Blood was stored at 8° C. prior to use.

The Thromboelastograph® sample cup is rotated ±5° about a vertical torsion wire suspended in the middle of the cup. As the hardening blood clot tugs on the torsion wire, the change in viscoelastic clot strength is monitored as a function of time. The time until the bimodal symmetric viscoelasticity curve's amplitude is 2 mm is referred to as R (minutes), and represents the initial detection of clot formation. The angle between the tangent to the curve and the horizontal is referred to as α (°), and is related to the rate of coagulation. The maximum amplitude of the curves is referred to as MA (mm) and represents the maximum clot strengths. Thromboelastograph® clotting parameters reported represent the mean of four reproducible trials. A summary of the hemostatic properties of metal-oxides with variable isoelectric points is described in Table 1.

Methods

The invention provides a method of producing a composition for modulating hemostasis, and also a method of modulating hemostasis comprising contacting blood with a composition of the invention. Compositions that modulate homeostasis can be prepared by the methods described in the Examples below, including aerosol synthesis and use of sol-gel chemistry. Sol-gel chemistry can be used to produce bioactive glass. By spraying the sol-gel solution down a hot furnace (e.g., 400° C.), spherical bioactive glass particles are produced. These bioactive glass particles can be as small as 10-50 nm in diameter, or smaller, or as large as about 100 µm or larger. In one embodiment, the particles are 50-200 nm in diameter.

Typically, the method of producing a composition of the invention involves starting from a bioglass sol, wherein the solvent is ethanol (or another solvent that can dissolve precursors and has a low boiling point). A block copolymer can be used as all additive to provide a pore-forming gent.

In some embodiments, such as the freezing method, the ideal solvent is water rather than ethanol because the melting point of ethanol is very low. The difference in solvent typically calls for some difference in the method. For example, most PEO—PPO-PEO block copolymers cannot dissolve in water. Second, chitosan can be incorporated into the system because it doesn't dissolve in the ethanol, and chitosan plays an important role in modulating blood coagulation. In addition, the silica and phosphous precursors are different from

TABLE 1

Summary of Metal-Oxide Contact-Activated Coagulation

| Clotting Metric | Low-surface-area metal oxides | High-surface-area metal oxides |
|---|---|---|
| Onset of coagulation; R (min) Initially Positively Charged Metal Oxide | Coagulation onset time increased or of equal value compared to blood alone for positively charged surface, and slowest for the most positive surface | Coagulation onset time for positively charged surface similar to blood alone |
| Initially Negatively Charged Metal Oxide | Coagulation onset time reduced for negatively charged surfaces, and fastest for most negative substrate | Coagulation onset time reduced for negatively charged surfaces |
| Rate of coagulation post-initiation; α (°) Initially Positively Charged Metal Oxide | Positively-charged surfaces decelerate the rate of coagulation | Positively-charged surfaces decelerate the rate of coagulation |
| Initially Negatively Charged Metal Oxide | Negatively-charged surfaces accelerate the rate of coagulation | Negatively-charged surfaces accelerate the rate of coagulation in the presence of sufficient Ca2+ ions |

| Clotting Metric | Isoelectric Point Below the pH of Blood | Isoelectric Point Above the pH of Blood |
|---|---|---|
| Onset of coagulation; R (min) | Coagulation onset time reduced for negatively charged surfaces, and fastest for most negative substrate | Coagulation onset time increased or of equal value compared to blood alone for positively charged surface, and slowest for the most positive surface |
| Rate of coagulation post-initiation; α (°) | Negatively-charged surfaces accelerate the rate of coagulation | Positively-charged surfaces decelerate the rate of coagulation |
| Ultimate clot strength (MA) | Most negative oxide resulted in steongest blood clots and least negative oxide resulted in weakest blood clot | Induced blood clots are less than or equal in strength to naturally formed blood clots | those in an ethanol-based method and phosphorous oxide is not required in the starting sol, as would be the typical case when starting with a bioglass sol.

In some embodiments, the method of modulating hemostasis comprises decreasing blood coagulation time. In one embodiment, the time to initiate detectable coagulation (R), as measured by Thromboelastograph®, is less than 2 minutes, and can be less than 1.8 minutes. In another embodiment, the rate of coagulation ($\alpha$), as measured by Thromboelastograph®, is more than 50°. Coagulation rates of more than 55°, and of more than 65° have been achieved. In a further embodiment, the coagulation results in a maximum clot strength (MA), as measured by Thromboelastograph®, of 55 to 100 mm, and can be less than 75 nm. Alternatively, the modulating comprises increasing blood coagulation time. Increased coagulation time is desirable, for example, when clotting poses a health risk to the subject.

Applications of the Invention

Oxides with an isoelectric point below the pH of blood can be formulated for action to induce blood clot formation faster than blood would naturally do in the absence of an oxide-contact activator. The materials can be applied both externally and internally as agents to induce hemostasis and reduce the flow of blood in a particular area of the body.

Oxides with an isoelectric point above the pH of blood can be formulated to induce blood clot formation slower than blood would naturally do in the absence of an oxide-contact activator, and therefore would be suitable as passivated surfaces for medical devices. Thus, the invention provides a medical device and methods of coating a medical device with a composition of the invention. Coatings can be prepared from a composition in powder form or using sol-gel chemistry, using conventional methods known in the art. In one embodiment, the coating reduces coagulation of blood in contact with the device. The medical devices include, but are not limited to, arterial and venal stents, catheters, shunts, and any medical machinery that will contact blood during invasive medical procedures.

Oxides with an isoelectric point above the pH of blood can be formulated for devices that require a positively charged surface to interface with biological tissue and fluids.

Oxides with an isoelectric point below the pH of blood can be formulated for devices that require a negatively charged surface to interface with biological tissue and fluids.

When mixed with an ammonium phosphate buffer solution, a bioactive glass cement can be prepared with a controllable set time. Bioactive glass, and particularly, bioactive glass cement, can be prepared with a flexible morphology that allows for conformation and adhesion to any wound geometry. The bioactive glass cement can be molded in a variety of shapes that retain their mechanical integrity post-setting. The bioactive glass cements can accelerate the deposition of an apatite layer compared to the bioactive glass agent alone.

Mesoporous bioactive glass can be formulated as a rapid acting hemostatic agent. This material can predictably warm injured tissue to promote wound healing.

Mesoporous bioactive glass can be formulated to promote the formation of artificial bone. This same material can be used to generate tissue including, but not limited to, artificial skin and structural elements such as fibrin and collagen.

The internal porous architecture can be loaded with biologically relevant molecules and cofactors for controlled released during wound healing and body repair. These biologically relevant molecules and cofactors include, but are not limited to, phospholipids, blood coagulation factors, fibrin, collagen, blood clotting zymogens, silver ions, magnesium ions, and calcium ions.

The internal porous architecture can be loaded with antibacterial peptides and silver ions for a controlled release of antibacterial agents.

Non-porous bioactive glass can be formulated as a rapid acting hemostatic agent. This material can predictably warm injured tissue to promote wound healing.

Non-porous bioactive glass can be formulated to promote the formation of artificial bone. This same material can be used to generate tissue including, but not limited to, artificial skin and structural elements such as fibrin and collagen.

The hemostatic activity of bioactive glass can be controlled and optimized for a variety of wound healing scenarios by manipulating the ratio of Si to Ca in the chemical composition of both porous and non-porous bioactive glass.

The bone-generating activity of bioactive glass can be controlled and optimized for a variety of wound healing scenarios by manipulating the ratio of Si to Ca in the chemical composition of both porous and non-porous bioactive glass.

EXAMPLES

The following examples are presented to illustrate the present invention and to assist one of ordinary skill in making and using the same. The examples are not intended in any way to otherwise limit the scope of the invention.

Example 1

Hemostatic Activity of Bioactive Glass

Figure 1:
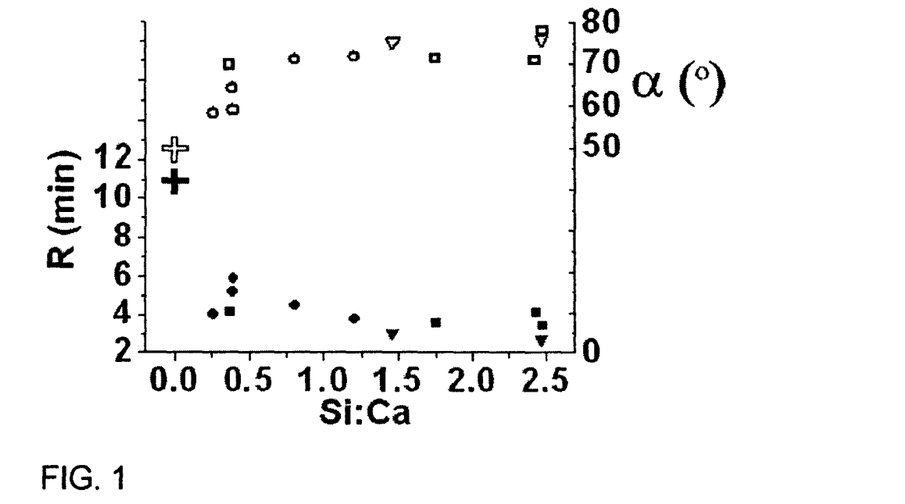
FIG. 1 is a plot of both clot detection time, R, (filled shapes) and rate of coagulation, α, (un-filled shapes) vs. BG Si:Ca. Data represents the mean of four trials. ■ Porous BG; ● Non-porous BG; ▼ Spherical BG; +No HA.
Figure 2:
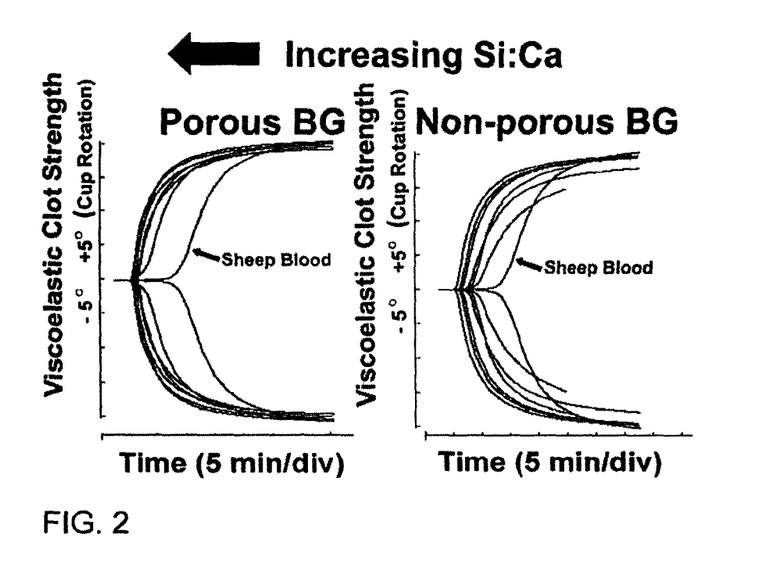
FIG. 2 is a Thrombelastograph®plot of bioactive hemostatic agents. Inner Thromboelastograph plot on both plots is sheep blood without a HA added.

The time until clot detection, R, decreases for increasing Si:Ca ratios in BG (FIGS. 1, 2). R is reduced by a factor of 2 when the Si:Ca ratio is doubled over the range studied.

BG can perform the dual role of providing surface area for thrombosis and supplying $Ca^{2+}$ ions; hence there will be an optimum ratio of $SiO_2$ to $Ca^{2+}$ ions, which are co-factors throughout the clotting cascade, for the fastest hemostatic response. The BG-induced coagulation rate, $\alpha$, increases with increasing Si:Ca ratios and maximizes for the same Si:Ca ratio as for the minimum R time (Si:Ca($R_{min}\alpha_{max}$)~2.5). All blood clots induced by BGs resulted in stronger than natural clots ($MA_{BG} \geq 62$ and $MA_{Natural} = 58$ dyn/cm$^2$.

Example 2

Formulation of Mesoporous Bioactive Glass

Figure 3:
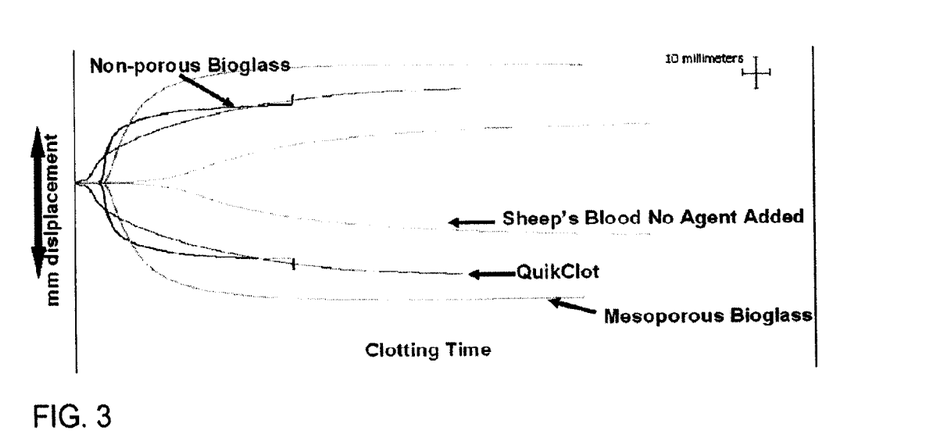
FIG. 3 is a Thrombelastograph® plot of bioactive glass, QuikClot™, and sheep's blood alone.
Figure 4:
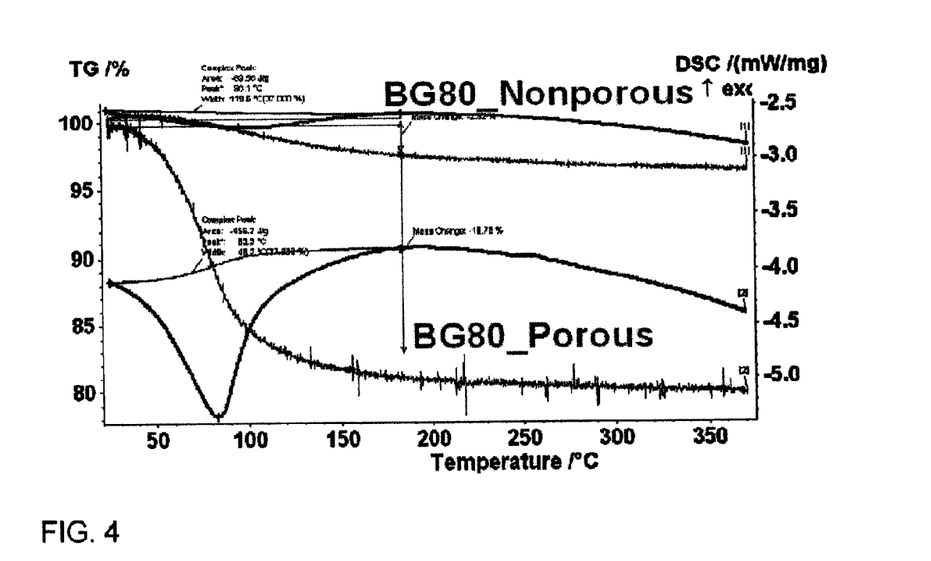
FIG. 4 is a thermogravimetric analysis and differential scanning calorimetry of the dehydration of porous and non-porous bioactive glass. 90 J/g (Non-porous Bioactive glass) and 450 J/g (Porous Bioactive glass).

The unique formulation of high surface area mesoporous bioactive glass that we have prepared has the ability to rapidly induce a blood clot when exposed to blood. In fact, the formulation we have prepared has a faster clotting time and results in a stronger clot than QuikClot™, the leading inorganic hemostatic agent currently available (see FIG. 3). Both the porous and non-porous formulations of bioactive glass possess this ability to rapidly promote blood coagulation. Because the porous and non-porous formulations of bioactive glass can be hydrated to different degrees, and consequently will deliver different amounts of heat upon hydration during medical application to a wound site, we can further tailor the rate of blood coagulation. Combinations of porous and non-porous bioactive glass can be formulated to the desired specifications of hydration and delivery of heat (see FIG. 4).

Example 3

Mesoporous Bioactive Glass with Varying Ratios of SiO2:CaO

Figure 5:
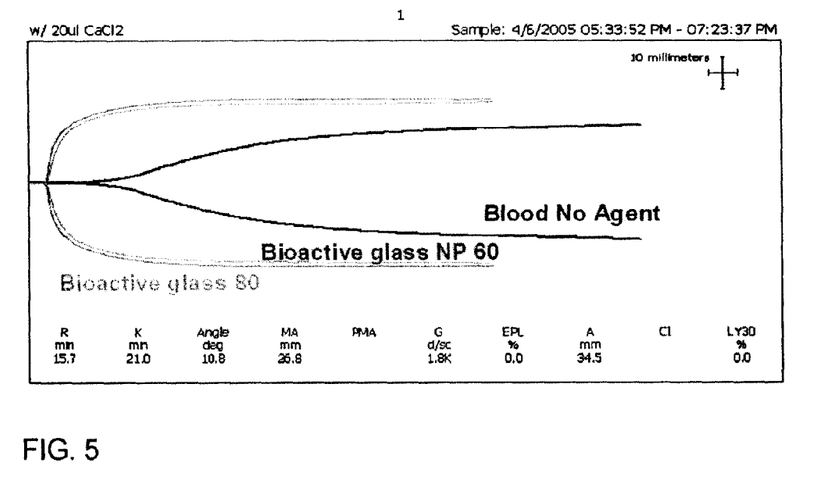
FIG. 5 is a Thrombelastograph® plot of mesoporous bioactive glass with varying SiO2:CaO ratios. BG 80 has a molar ratio of SiO2:CaO of 80:16. BG 60 has a molar ratio of SiO2:CaO of 60:16.
Figure 6:
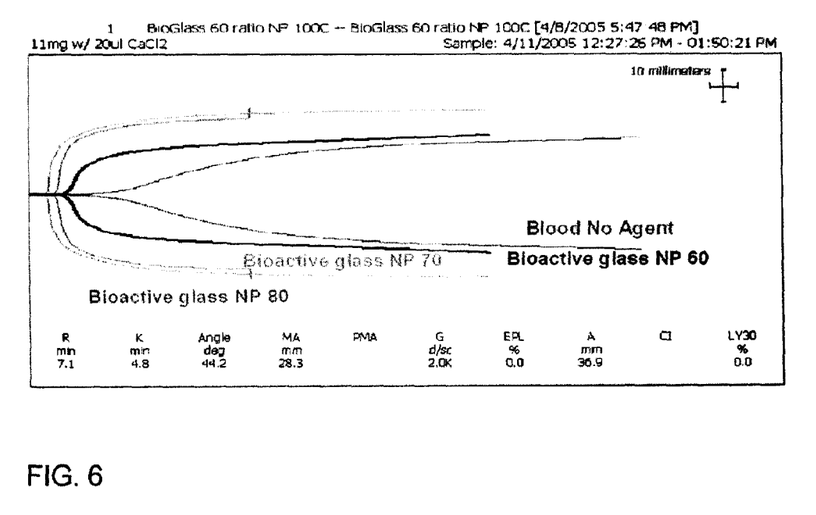
FIG. 6 is a Thrombelastograph® plot of non-porous bioactive glass with varying SiO2:CaO ratios. BG NP 80 has a molar ratio of SiO2:CaO of 80:16. BG NP 70 has a molar ratio of SiO2:CaO of 70:16. BG NP 60 has a molar ratio of SiO2:CaO of 60:16.

This example shows that one make the bioactive glass with varying ratios of SiO2:CaO. At higher SiO2:CaO ratios (more silica), the material tends to clot blood faster. This is illustrated in both FIGS. 5 and 6. As the amount of SiO2 relative to the amount of CaO is reduced, the kinetics of clot formation are much slower. The difference in clotting kinetics between two bioactive glass samples with different SiO2:CaO is more pronounced with the non-porous samples. The mesoporous bioactive glass is a faster clotting agent than the non-porous samples, but the difference between samples is greater within the non-porous samples.

Figure 7:
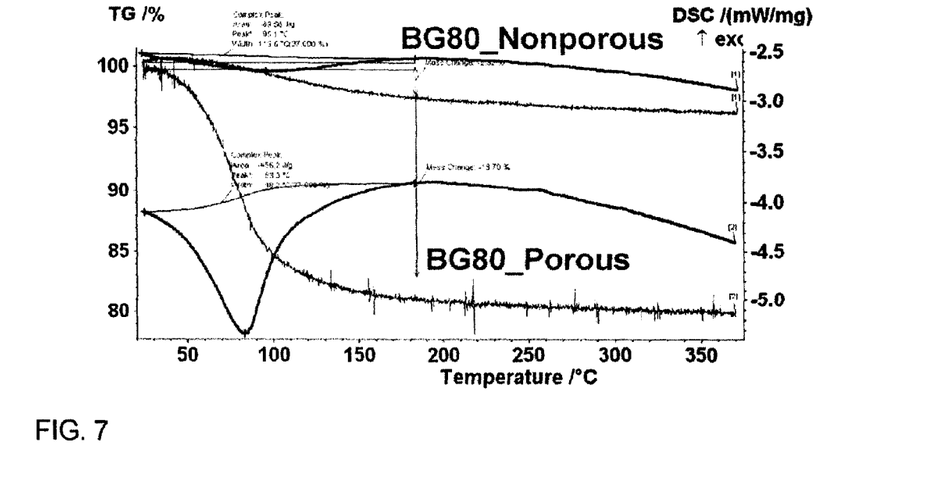
FIG. 7 is a thermogravimetric analysis and differential scanning calorimetry of the dehydration process for a hydrated mesoporous bioactive glass and a non-porous bioactive glass.
Figure 8:
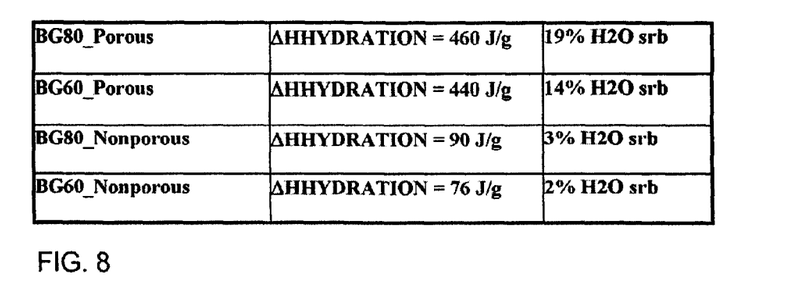
FIG. 8 is a compilation of the heat of hydration and hydration capacity of bioactive glass. BG80 has a molar ratio of SiO2:CaO of 80:16. BG60 has a molar ratio of SiO2:CaO of 60:16.

This example also shows that one can use combinations of porous and non-porous bioactive glass, as well as composites with multiple bioactive glasses of different SiO2:CaO ratios, to achieve any desired hydration capacity and heating response when in contact with blood (see FIGS. 7 and 8).

Example 4

Spherical Bioactive Glass

Figure 9:
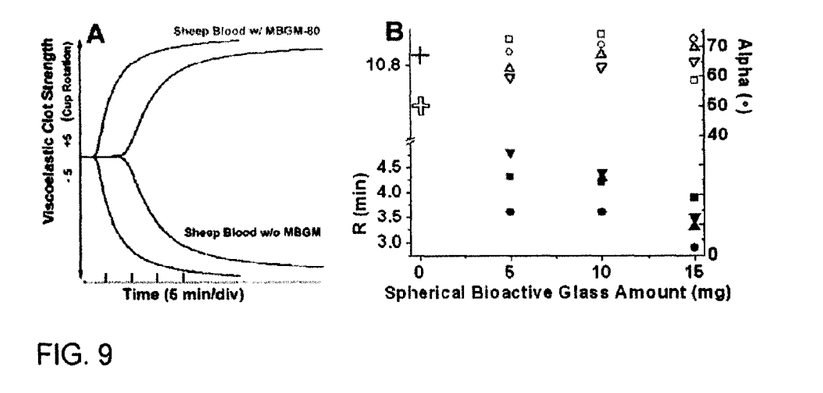
FIG. 9A shows a Thromboelastograph® plot of the hemostatic activity MBGM-80 induced coagulation vs. blood w/o MBGM-80.
FIG. 9B shows a plot of both clot detection time, R, (filled shapes) and rate of coagulation, α, (un-filled shapes) vs. amount of mesoporous bioactive microspheres. Data represents the mean of four trials. ■ MBGM-60, ● MBGM-80, ▲ MBGM-60 Non-porous, ▼ MBGM-80 Non-porous, +Sheep Blood w/o MBGM.

Spherical Bioactive glass is produced by an aerosol assisted method and with the same sol-gel precursor solution employed for bioactive glass previously described. Spherical bioactive glass accelerates the formation of a contact-activated clot. The activity of bioactive glass is dependent on the relative amount of contact activating agent to the surrounding blood volume (FIG. 9).

Example 5

Host-guest Composites

The porous architecture of mesoporous bioactive glass is ideal for the controlled release of biomolecules. These molecules can be immobilized on the oxide surface of bioactive glass or solvated with surfactants inside the pores, or loaded alone in die pores. Each of these formulations will have a unique release profile with regard to concentration and rate of release. The combination of porous bioactive glass and biomolecules is referred to as a host-guest composite.

Host-guest composites can also be prepared to release ions including, but not limited to, silver, magnesium and calcium ions. Silver ions have been shown to be antibacterial at parts per billion concentration in biological fluids. Magnesium and calcium ions are essential cofactors during the coagulation of blood. Certain formulations of porous bioactive glass can also sequester magnesium and calcium from blood to delay the coagulation response.

Synthesis

Mesoporous bioactive glasses (MBGs) were synthesized by co-assembly of a BG sol with a triblock copolymer poly (ethylene oxide)-poly(propylene oxide)-poly(ethylene oxide) as the structure-directing agent through an evaporation-induced self-assembly (EISA) process. The dried gel was calcined at high temperature to remove the block copolymer and form mesopores. The final MBGs were ground into powders. The as-calcined MBGs have more accessible mesopore surface area and ordered pore structure. In vitro study showed a greater bone-forming bioactivity than conventional sol-gel derived BGs by fast formation of an amorphous bioactive HA layer.

Example 6

Bioactive Glass Cements

Bioactive glass cements were prepared by mixing bioactive glass powders with an ammonium phosphate buffer solution. The liquid component of MBGCs, an ammonium phosphate buffer solution, was prepared by dissolving 60.1 g $(NH_4)_2HPO_4$ and 5.0 g $NH_4H_2PO_4$ in 100 mL water. The pH of the resulting solution was ~7.3. MBGC cements were made by mixing the solid and liquid components at the ratio of 1 g to 1 mL. The cements were kept in the ambient environment to set. Before setting fully, they were soft enough to be kneaded or molded. Structural characterizations were typically carried out at ~1 h after the mixing of the solid and liquid components of MBG, and no structural changes were observed after 1 h after mixing.

The assessment of the in vitro bioactivity of bioactive glass powders and cements was carried out in SBF at 37° C. SBF contained 142.0 mM $Na^+$, 5.0 mM $K^+$, 1.5 mM $Mg^+$, 2.5 mM $Ca^{2+}$, 147.8 mM $Cl^-$, 4.2 mM $HCO_3^-$, 1.0 mM $HPO_4^{2-}$, and 0.5 mM $SO_4^{2-}$. Its chemical composition is similar to that of human plasma. The solution had a pH of 7.3-7.4 and was kept at 37° C. before use.

Example 7

Surface Area Measurements of Mesoporous Bioactive Glass

Figure 10:
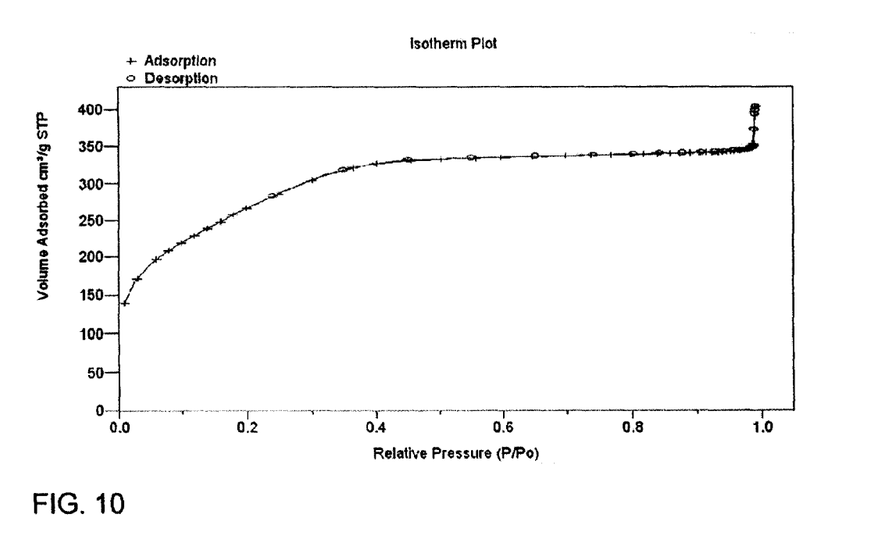
FIG. 10 shows BET adsorption-desorption isotherm of bioactive glass.
Figure 11:
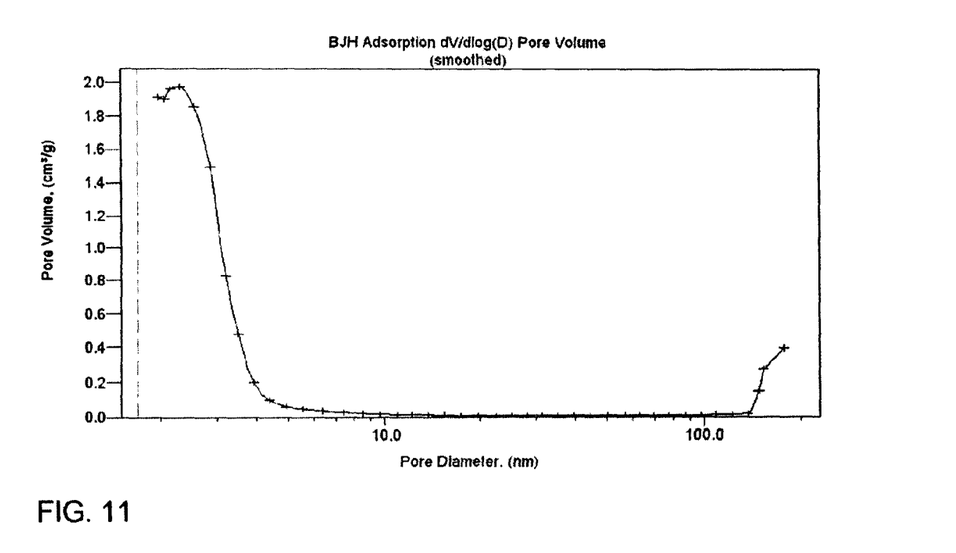
FIG. 11 shows pore size distribution of mesoporous bioactive glass.

This example presents data on the surface area measurements that have been made of the mesoporous bioactive glass of the invention. In FIG. 10, the adsorption-desorption isotherm is presented. The lack of hysteresis suggests a channel-like structure without internal cages. This adsorption-desorption isotherm can be used to calculate the pore size distribution of the mesoporous bioactive glass based on the BJH model. A plot of the pore size distribution is illustrated in FIG. 11.

Figure 12:
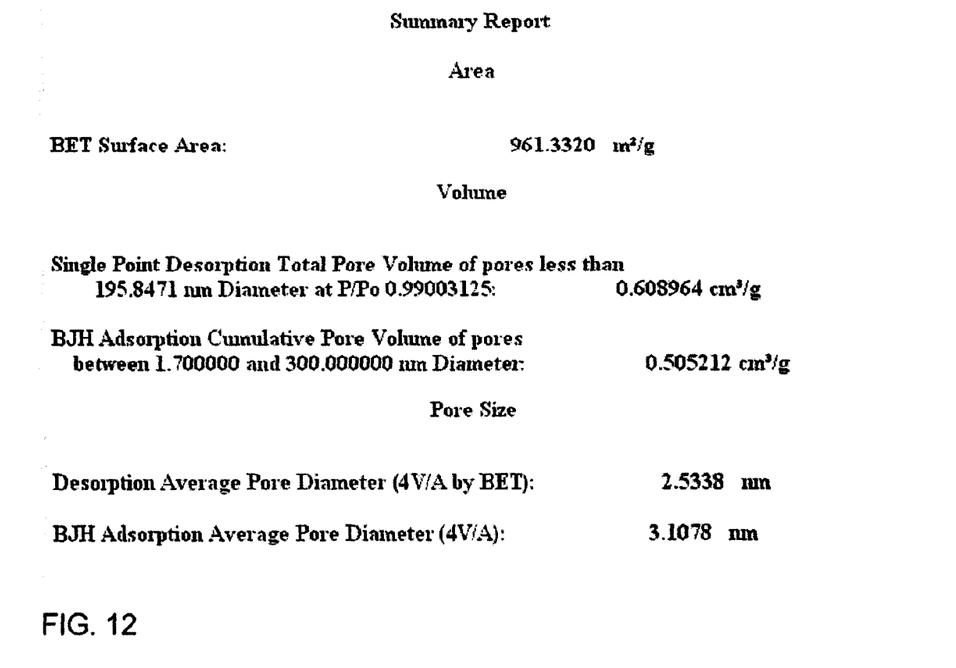
FIG. 12 shows BET surface area and pore diameter calculations.

The calculated surface area of mesoporous bioactive glass is displayed in FIG. 12. Bioactive glass can be formulated with a surface area ranging from 300 $m^2/g$ to 1000 $m^2/g$. The sample that was used for the measurements described in this example had a surface area of 960 nm/g. The internal pore diameter was calculated to be 3.1 nm based oil the BJH model and 2.5 nm based on the BET model.

Example 8

Bone-generating Activity of Bioactive Glass

The assessment of the in vitro bioactivity of bioactive glass powders and cements was carried out in simulated body fluids (SBF) at 37° C. SBF contained 142.0 mM $Na^+$, 5.0 mM $K^+$, 1.5 mM $Mg^{2+}$, 2.5 mM $Ca^{2+}$, 147.8 mM $Cl^-$, 4.2 mM $HCO_3^-$, 1.0 mM $HPO_4^{2-}$, and 0.5 mM $SO_4^{2-}$. Its chemical composition is similar to that of human plasma. The solution had a pH of 7.3-7.4 and was kept at 37° C. before use.

Figure 13:
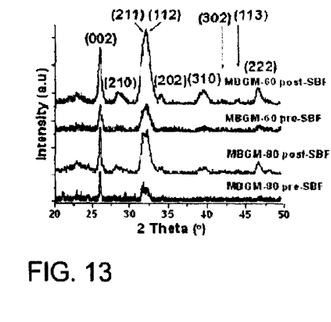
FIG. 13 shows wide angle x-ray diffraction of bioactive glass substrates pre- and post-immersion in simulated body fluids for 1 hour.

The in vitro assessment of in vivo bone-generating bioactivity is typically conducted by monitoring the formation of hydroxyapatite on die surface of bioactive glass after immersion in SBF. After mixing the bioactive glass powder with the ammonium phosphate buffer solution, weak x-ray diffraction peaks at 2θ=26° (002) and 32° (211) corresponding to hydroxyapatite are observed. The broad peak at 2θ=23° is due to the amorphous nature of the bioactive glass walls (FIG. 13). The average hydroxyapatite crystal size nucleated after immersing BG60:36:4 in simulated body fluids for one day is 37 nm. The average hydroxyapatite crystal size nucleated after immersing BG80:16:4 in simulated body fluids for one day is 32 nm. Faster rates of hydroxyapatite were observed with BG60:36:4 compared to BG80:16:4.

Example 9

Isoelectric Point, Fast Acting Clotting Agents, and Passivated Medical Device Surfaces As described in U.S. provisional patent application No. 60/668,022, filed Apr. 4, 2005, we have identified four critical materials parameters that can be used to predict the hemostatic response for exposing a given oxide to blood. We have shown that blood coagulation can be induced rapidly through the dehydration of blood, application of an appropriate amount of heat, and by delivering ions, like calcium, that are cofactors in the blood coagulation network. Oxides with a surface charge will also induce a coagulation response. More specifically, the isoelectric point is the underlying principle effecting the surface charge induced contact activation coagulation response.

Figure 14:
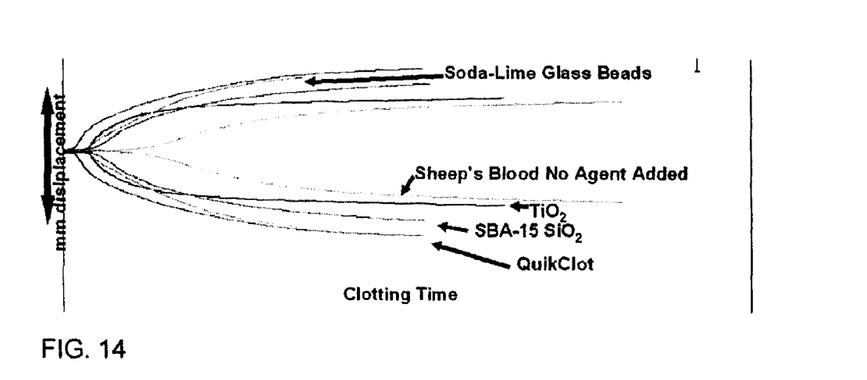
FIG. 14 is a Thrombelastograph® plot of oxides with an isoelectric point below the pH of blood.
Figure 15:
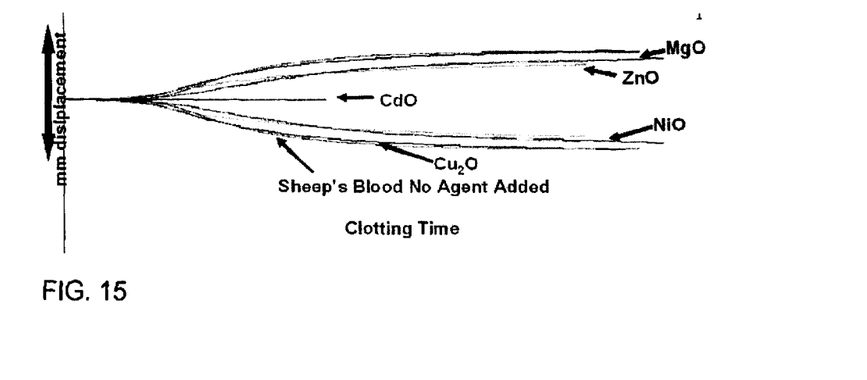
FIG. 15 is a Thrombelastograph® plot of oxides with a isoelectric point above the pH of blood.

Every oxide material will possess an initial surface charge that is a function of both the isoelectric point of the material and the pH conditions of the immersing solution (see FIG. 14). By observing the rate of coagulation of blood upon exposure to a variety of inorganic oxides, we have observed that those materials with an isoelectric point below the pH of blood accelerate the coagulation response (see FIG. 14). Those materials with an isoelectric point above the pH of blood are observed to decelerate the coagulation response (see FIG. 15).

Designing rapid acting hemostatic agents requires an optimization of the four material parameters already identified: isoelectric point, hydration capacity, thermal application (heat), and control of the local electrolyte conditions. Similarly, designing passivated medical device surfaces for contact with blood requires a related, albeit opposite, optimization of these material parameters compared to a fast acting clotting agent. By selecting oxides of varying isoelectric points, it is possible to modulate the blood coagulation response from spontaneous coagulation to inhibition of coagulation. This control over the blood response is unique to inorganic oxides and offers major advantages over current organic based hemostatic technology. This relationship between isoelectric point and coagulation provides for the design of new bioactive glass compositions tailored to desired objectives in the regulation of hemostasis.

Example 10

Isoelectric Point and Low-surface-area Metal Oxides

Figure 16:
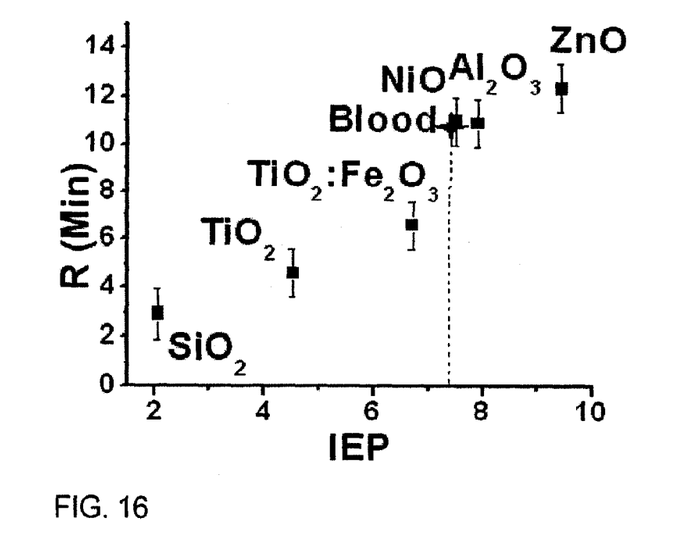
FIG. 16 shows R (min), onset of clot detection, versus the metal oxide's isoelectric point for low-surface area metal oxides.

It is well accepted that negatively charged surfaces activate the intrinsic pathway of the blood clotting cascade. The $SiO_2$ glass beads, which have the lowest isoelectric point (IEP=2.1) of all the low-surface-area oxides analyzed, initiated the formation of a detectable blood clot on average 2.9 min after exposure to sheep blood. Because this material has the lowest isoelectric point, under physiological conditions (pH=7.3-7.4), $SiO_2$ substrates will initially posses the greatest negative surface-charge density compared to the other oxides tested. The time until clot detection increases with the increasing isoelectric point of the low-surface-area materials studied (FIG. 16). NiO has the isoelectric point that is closest to the pH of blood, and the average clot time induced by NiO is nearly indistinguishable from that of blood in its absence ($R_{NiO}$=11 min and $R_{BloodAlone}$=10.9 min). ZnO has the highest isoelectric point of the materials studied (IEP=9.5) and was observed to actually delay the time until blood clot detection by about 1.5 min compared to sheep blood alone.

Figure 17:
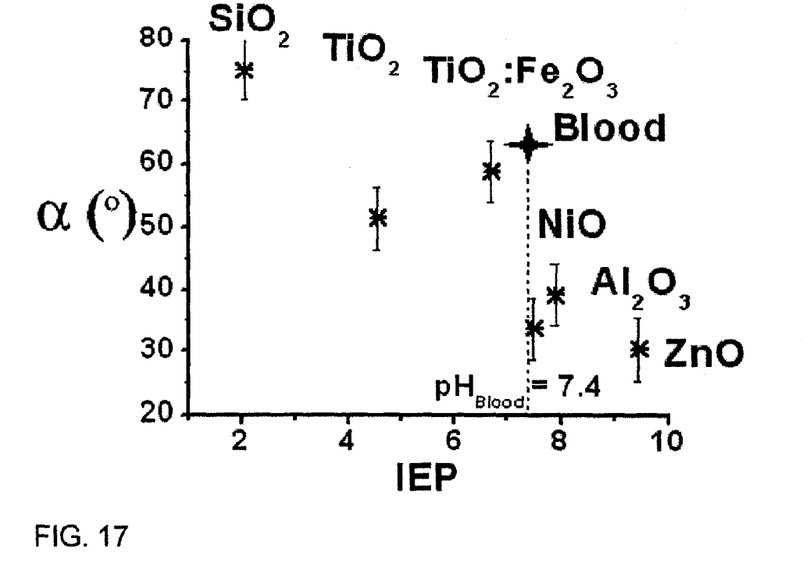
FIG. 17 shows α (°), rate of coagulation, versus the metal oxide's isoelectric point, for low-surface area metal oxides.

The fastest rate of coagulation, $\alpha$ (°), for the low-surface-area metal oxides, was observed with the $SiO_2$ glass beads ($\alpha$=75.2°, IEP=2.1), which initially posses the most negative surface in blood compared to the other low-surface-area metal oxides studied. (FIG. 17). The slowest rate of coagulation was observed when ZnO was introduced to sheep blood ($\alpha_{Blood}$=50.2°; $\alpha_{ZnO}$=30.4°). ZnO possesses the maximum positive surface charge when immersed in blood. All of the oxides with an isoelectric point above the pH of blood were observed to decelerate the rate of coagulation compared to blood alone, and in particular, NiO, which has the closest isoelectric point to the pH of blood but will be positively charged after immediately contacting blood, was observed to reduce the rate of coagulation.

From the foregoing it will be appreciated that, although specific embodiments of the invention have been described herein for purposes of illustration, various modifications may be made without deviating from the spirit and scope of the invention.

What is claimed is:

1. A device adapted for treatment of wounds comprising a hemostatic composition disposed as a coating on the device, the hemostatic composition comprising a hemostatically effective amount of kaolin hydrated from 0.1% to 25% and an inorganic salt, wherein the hemostatic composition has an isoelectric point, as measured in a calcium chloride solution, below the pH of blood, and wherein the hemostatic composition does not include a hemostatically effective amount of a zeolite.

2. The device of claim 1, wherein the hemostatic composition has an isoelectric point below 7.3.

3. A method of modulating hemostasis, the method comprising contacting a wound with a device of claim 1, wherein said contacting is sufficient to decrease blood coagulation time.

4. The device of claim 1, wherein the hemostatic composition further comprises an oxide selected from the group consisting of calcium oxide, sodium oxide, magnesium oxide, zinc oxide, phosphorus oxide and alumina.

5. The device of claim 1, wherein the inorganic salt comprises a divalent ion selected from the group consisting of zinc, copper, magnesium, calcium and nickel.

6. The device of claim 1, wherein the inorganic salt is selected from the group consisting of: CaO, $CaCl_2$, $AgNO_3$, $Ca(NO_3)_2$, $Mg(NO_3)_2$, $Zn(NO_3)_2$, $NH_4NO_3$, AgCl, $Ag_2O$, zinc acetate, magnesium acetate, calcium citrate, zinc citrate, magnesium citrate, magnesium chloride, magnesium bromide, zinc chloride, zinc bromide, calcium bromide, calcium acetate and calcium phosphate.

7. A device adapted for treatment of wounds comprising a hemostatic composition disposed as a coating on the device, the hemostatic composition comprising a hemostatic agent and an inorganic salt, the hemostatic agent consisting essentially of a hemostatically effective amount of kaolin hydrated from 0.1% to 25%, wherein the hemostatic composition has an isoelectric point, as measured in a calcium chloride solution, below the pH of blood.

8. The device of claim 7, wherein the hemostatic composition has an isoelectric point below 7.3.

9. A method of modulating hemostasis, the method comprising contacting a wound with a device of claim 7, wherein said contacting is sufficient to decrease blood coagulation time.

10. The device of claim 7, wherein the inorganic salt comprises a divalent ion selected from the group consisting of zinc, copper, magnesium, calcium and nickel.

11. The device of claim 7, wherein the inorganic salt is selected from the group consisting of: $CaCl_2$, $AgNO_3$, $Ca(NO_3)_2$, $Mg(NO_3)_2$, $Zn(NO_3)_2$, $NH_4NO_3$, AgCl, $Ag_2O$, zinc acetate, magnesium acetate, calcium citrate, zinc citrate, magnesium citrate, magnesium chloride, magnesium bromide, zinc chloride, zinc bromide, calcium bromide, calcium acetate and calcium phosphate.

12. The device of claim 1, wherein the hemostatic composition initiates detectable coagulation (R) in 2 minutes or less upon contacting the wound.

13. The device of claim 1, wherein the hemostatic composition produces a rate of coagulation ($\alpha$) of 50° or more upon contacting the wound.

14. The device of claim 1, wherein the hemostatic composition produces a maximum clot strength (MA) of 55 mm to 100 mm upon contacting the wound.

* * * * *